United States Patent
Lolagne

[11] Patent Number: 5,865,835
[45] Date of Patent: Feb. 2, 1999

[54] FORCEPS

[76] Inventor: Fritz Lolagne, 292 Avenue John Brown Bourdon, Port au Prince, Haiti

[21] Appl. No.: 825,757

[22] Filed: Apr. 3, 1997

Related U.S. Application Data

[63] Continuation-in-part of Ser. No. 375,423, Jan. 18, 1995, Pat. No. 5,618,305, which is a continuation-in-part of Ser. No. 252,209, Jun. 1, 1994, abandoned, which is a continuation-in-part of Ser. No. 94,627, Jul. 21, 1993, abandoned.

[51] Int. Cl.$^6$ .................................................. A61B 17/00
[52] U.S. Cl. .......................................... 606/205; 606/148
[58] Field of Search ................................... 606/139–148, 606/205–210

[56] References Cited

U.S. PATENT DOCUMENTS

| | | |
|---|---|---|
| 2,397,823 | 4/1946 | Walter . |
| 2,642,871 | 6/1953 | Thuerig . |
| 3,828,791 | 8/1974 | Santos . |
| 4,226,241 | 10/1980 | Walker, Jr. . |
| 5,067,958 | 11/1991 | Sandhaus . |

FOREIGN PATENT DOCUMENTS

| | | |
|---|---|---|
| 0635243 | 1/1995 | European Pat. Off. . |
| 145976 | 3/1961 | U.S.S.R. . |
| 219095 | 8/1968 | U.S.S.R. . |
| 1321409 | 8/1984 | U.S.S.R. . |
| 2 210 574 | 6/1989 | United Kingdom . |
| 2 227 200 | 7/1990 | United Kingdom . |

OTHER PUBLICATIONS

Instrumentation for the operating room, Shirley M. Brooks, R.N., B.A., St. Louis, 1978, p. 188.

*Primary Examiner*—Michael Powell Buiz
*Assistant Examiner*—Nancy Mulcare
*Attorney, Agent, or Firm*—Richard C. Litman

[57] ABSTRACT

A forceps having a closed loop defined by the ends of beveled grasping tips attached to a pair of jaws of locking forceps in a closed position, a series of mating serrations on the jaws ending proximate the loop, and having an hourglass shape when viewed in profile. The forceps reduces slippage of the vagus by a raised bevelled ridge on the closed loop facing inward towards the aperture. The oval-shaped and hourglass profiled aperture defined by the closed loop is shaped and sized to permit a surgeon to firmly grasp the vagus nerve, and to elevate it up and out of the incision area, in order to facilitate the remaining procedure. The preferred aperture opening is defined by the loop having a 3 mm transverse inner diameter and 4 mm longitudinal inner diameter. The hourglass profile allows the vagus nerve to rest in a transverse groove of the tip, defining the constriction found in the hourglass profile. The mating serrations, which form a line following the lengthwise extension of the instrument, provide a continuous, firmly closed line behind the loop and define the longitudinal axis of the forceps. The arms of the forceps are approximately 11 centimeters long, thereby providing additional reach necessary in surgical interventions in the lower esophagus and stomach where the vagus is present.

8 Claims, 5 Drawing Sheets

FORCEPS

CROSS-REFERENCE TO RELATED APPLICATION

This application is a Continuation-in-Part of application Ser. No. 08/375,423, filed Jan. 18, 1995, issued as U.S. Pat. No. 5,618,305, which was a Continuation-in-Part of application Ser. No. 08/252,209, filed Jun. 1, 1994, now abandoned, which was a Continuation-in-Part of application Ser. No. 08/094,627, filed Jul. 21, 1993, now abandoned.

BACKGROUND OF THE INVENTION

1. Field of the Invention

The present invention relates generally to surgical implements for griping tissue, and more particularly to forceps used to grasp the vagus nerve while conducting surgical interventions in the lower esophagus or stomach.

2. Description of Related Art

A commonly used instrument in performing surgical interventions is a standard forceps, such as Allis forceps. The standard forceps comprises a scissor-like construction that includes a locking mechanism for the two arms at the handle end. The grasping tips, at the ends of the arms opposite the handles, have mating sawtooth extensions, which meet in a line perpendicular to the lengthwise extension of the instrument and are used to clamp onto tissue.

Because of the large, flattened area defined by the tips of standard forceps, additional tissue is often grasped during a surgical operation and elevated along with the target tissue to be grasped. For example, the vagus nerve, like many other nerves, lies in close proximity to vascular tissue such as veins and arteries, and is, along with such other tissues, cloaked in mesenteric tissue. Moreover, a nerve, although having moderate resilience to stretching thereby allowing an instrument to be placed loosely beneath the nerve to retract it from a surgical site, is particularly vulnerable to crushing, the consequence of which may include faulty neurological transmission due to an interruption of electrical conduction caused by irreparably crushing of cells. Because the vagus nerve has a large diameter, exceeding 4 mm in places, to pull it up and out of an incision area with the larger, flattened areas of the tips of the closed jaws of the a standard forceps would likely cause crushing, and at best pinching as a result of the nerve bending over the edged surfaces of the jaws. Thus, the large ends and clamping structure defined by the standard forceps is particularly unsuited for use to grasp and retract the vagus nerve. Moreover, due to the open ends of the grasping tips, tissue often slips out of the grasp of the instrument when the nerve is lifted clear. In each case, the surgeon is required to recapture the tissue, and recommence this part of the procedure. Such imprecision and slippage renders the procedure longer, and more difficult to conduct than if a forceps with a design more specific to the procedure were used.

Another common instrument is the rod clamp used with a threaded rod in orthopedic surgery. The clamp has a blunt, widened tip, defining an aperture for passage and clamping of the rod. Whereas the aperture may allow passage of any tubular item, the blunt, wide tip and short jaws prevent the rod clamp from use for fine manipulations in a wound site, such as finding a nerve in an already occluded area. The short, wide, blunt jaws would act to block the view of the wound site. Moreover, because the end of the jaws are very near the pivot stud joining the two arms of the clamp to allow a scissoring action of the clamp, the arms must be widely spread apart for open the jaws to open sufficiently at the opposite end to accept the vagus nerve. This would require a surgeon to have a very large hand span in order to operate with difficulty at best.

Several attempts have been made to overcome the problems associated with the use of standard forceps in procedures requiring manipulation of stranded or tubular tissues. U.S. Pat. No. 2,397,823, issued to Carl W. Walter, on Apr. 2, 1946, discloses a forceps intended to be capable of grasping a wide variety of objects. This forceps has a elongated "pistol-grip" handle. It is oriented at an angle of at least 45 degrees relative to a gripping portion of the device. The forceps of Manual V. Santos shown in U.S. Pat. No. 3,828,791 issued Aug. 13, 1974 utilizes a similar functional design. Consequently, minute manipulations of tissue during a surgical procedure would be cumbersome at best, and dangerous at worst.

Moreover, the Walter forceps is shown to have serrations on the very tip. Such serrations, while providing additional gripping friction, would necessarily cause destruction of surrounding tissue. Also, the presence of these serrations clearly indicate that this forceps has a clamping hole substantially recessed from the end of the device, in stark contrast with applicant's own invention. Use of such a device in a retraction of the vagus nerve would require a larger incision than necessary to pass the device into the wound site sufficiently far for the clamping hole to engage the vagus nerve; moreover, it would cause tissue damage when the device is closed and clamped around the nerve. It would also make the lifting of the vagus nerve impossible without substantial destruction of surrounding, additional tissue caught in the large extension of the forceps' tips beyond the clamping hole, in turn resulting in additional, unwarranted procedure length, trauma, and danger.

Both the Santos and Walters devices fail to have a beveled rim around the edge of the hole nearer its grasping end to provide effective gripping for lifting stranded tissue such as the vagus nerve. Instead, the Walters device has "arcs of different curvature" disposed around the rims of recesses in the jaws, which are described as including an "almost blade-like inner edge." Such bladed arcs would tend to cut tissue held, making holding of tissue impractical and dangerous. In fact, the forceps is intended for use with objects other than tissue, such as needles and swabs. Importantly, the literature describing the use of this device does not even mention its use for vagus retraction and lifting.

U.S. Pat. No. 2,642,871, issued to Joseph Theurig, on Jun. 23, 1953, discloses a forceps suitable for grasping tubular objects, such as syringes. The forceps has a clamping aperture described and depicted as comprising "transverse inverted obtuse angular meeting faces." The difficulty concomitant of using such a device in lifting the vagus nerve is substantial. Because the aperture is not curved to the shape of a tubular strand such as the vagus nerve, the vagus nerve would tend to both slide laterally and rotate within the aperture, if not be pinched during full closure with the tips contacting one another. Making the device smaller, so that the device would immovably hold the vagus, would result in failure of the device to close completely, as shown in FIG. 4 of the Theurig patent. Without complete closure, the device would tend to allow undesired release of the vas deferens during required lifting. The Theurig forceps also lacks a beveled rim around the edge of the hole nearer its grasping end to provide effective gripping of tubular tissue. Notably, the literature referring to the use of this device does not even mention use for retracting the vagus nerve.

U.S. Pat. No. 5,067,958, issued to Jeffrey J. Sandhaus, on Nov. 26, 1991, demonstrates a complicated apparatus intended to be used in procedures for implanting locking clips for clamping and occluding tubular vessels, such as the vas deferens during a vasectomy. Whereas the device includes a curved clamping hole appropriate for immovably holding a tublar vessel with the tips contacting one another, the clamping hole is relatively far removed (in comparison with applicant's own invention) from the end of the apparatus, as shown in FIG. 45 of the Sandhaus patent. Use of such a device in a vagus lifting procedure would cause tissue damage while the device is passed sufficiently far into the wound site for the clamping hole to engage the vagus; cause tissue damage when the device is closed and clamped around the vagus nerve; and, make the procedure's lifting of the vagus impossible without substantial destruction of surrounding tissue, because of additional tissue caught in the large extension of the forceps' tips beyond the clamping hole. The Sandaus forceps also fails to provide a beveled rim around the edge of the hole nearer its grasping end to provide effective grasping during lifting of a tubular tissue to prevent lateral slippage of the instrument along the tubular tissue.

British Patent No. 2,227,200, issued to Malcolm Charles Holbrook, on Jul. 25, 1990, discloses a forceps used for holding a catheter or organ duct during the course of a surgical procedure. This forceps has a three-millimeter clamping hole centered five millimeters from the end of the forceps, a relatively large distance (many times as large as the applicant's own invention) that makes the device unusable for the vagus retracting procedure. This forceps was designed for its invisibility to X-rays used during a surgical procedure, and not for use in vagus retractions. The Holbrook forceps also lacks a beveled rim around the edge of the hole nearer its grasping end to provide effective gripping a vagus nerve. The large end design of the Holbrook patent has a clasping, rather than grasping function, and is unsuitable for use with nerve tissue due to the risk of crushing.

Other inventions have similar disadvantages. UK Patent Application No. 2 210 574 to James Richard Smith describes a forceps with triangular head, including a bridge defining an aperture for gripping a suture needle. None of the devices shown therein can grasp a vagus nerve without clamping down upon it, causing crushing. This disadvantage is likewise true of the surgical forces with notches for accommodating suture needles as shown in U.S. Pat. No. 4,26,241 issued Oct. 7, 1980 to William E. Walker, Jr. USSR Patent No. 145,976 shows a pair of forceps, having serated teeth provided along a substantial portion of the tip before an aperture is provided. Like the previously mentioned devices, the serated tip increases the risk of crushing and increased trauma due to insertion of the tip into surrounding tissue. USSR Patent No. 1321409 shows a pair of forceps, having semi-circular jaws with intermittant sets of serated teeth. USSR Patent No. 219095 shows a pair of forceps, having open-ended tipped jaws moulded to the same shape as a prosthesis for the long branch of the anvil in the ear; the open-ended tips are unsuitable for retracting a tubular tissue, allowing it to slip from the open-ends.

Finally, European Patent Application by applicant Fritz Lolagne published Jan. 25, 1995, contemplates forceps generally sized to closely conform to the cross-sectional shape of the vas deferens and vagus nerve, providing preferred diameters of the enclosing aperture at the tip of the forceps to be 0.40 centimeters in length and 0.30 centimeters in width. The application fails to disclose the crested ridge or the hourglass profile of the present invention.

None of the above inventions and patents, taken either singularly or in combination, is seen to describe the instant invention as claimed. Thus, a forceps solving the aforementioned problems is desired.

SUMMARY OF THE INVENTION

The forceps of the present invention resolves the problems inherent in the prior art by means of a small end structure, comprising an oval-shaped, closed loop, having an hourglass shape when viewed in profile. The closed loop is defined by the ends of beveled grasping tips attached to a pair of jaws of locking forceps in a closed position, a series of mating serrations on the jaws ending proximate the loop. The loop is approximately 0.60 centimeters in longitudinal outer diameter (from distalmost tip to first serration) and 0.40 centimeters in transverse outer diameter (from outside surface to outside surface). The forceps further reduces slippage of the vagus by a raised bevelled ridge on the closed loop facing inward towards the aperture.

The oval-shaped and hourglass profiled aperture defined by the closed loop is shaped and sized to permit a surgeon to firmly grasp the vagus nerve, and to elevate it up and out of the incision area, in order to facilitate the remaining procedure. The preferred aperture opening is defined by the loop having a 3 mm transverse inner diameter and 4 mm longitudinal inner diameter. The hourglass profile allows the vagus nerve to rest in a transverse groove of the tip, defining the constriction found in the hourglass profile. The mating serrations, which form a line following the lengthwise extension of the instrument, provide a continuous, firmly closed line behind the loop and define the longitudinal axis of the forceps. The arms of the forceps are approximately 11 centimeters long, thereby providing additional reach necessary in surgical interventions in the lower esophagus and stomach where the vagus resides.

Thus, the present invention provides numerous advantages over the standard forceps design used in conducting vasectomies, including but not limited to:

(1) reducing the risk of slippage of the vagus nerve due to the oval-shaped grasping opening, thereby reducing the time needed to conduct the procedure so the operation can be accomplished more safely;

(2) a smaller incision in the area of the vagus nerve than that necessary with the standard forceps due to a decreased tip size, thereby reducing risk of hemorrhage following the procedure; and, (3) minimizing the risk of pinching the vagus nerve due to the properly dimensioned opening and the hourglass profile, which allows the nerve to lie across the jaws on a more gentle arc.

Accordingly, it is a principal object of the invention to reduce the risk of slippage of the vagus during retraction by providing an oval-shaped grasping aperture sized to the diameter of the vagus nerve, which allows a user to grasp and lift the vagus nerve more easily and securely than does the standard design.

It is another object of the invention to reduce the time needed to conduct a procedure by reducing the lost time due to slippage of the nerve during a procedure, as compared to using the standard forceps design, by providing a surgical clamp having a closed ended loop.

It is a further object of the invention to reduce damage to surrounding tissue by having a very short tip which encloses the vagus nerve without unduly grasping or otherwise disturbing surrounding connective and other tissue.

Still another object of the invention is to provide a tip which allows the vagus nerve to rest in a groove during lifting of the vagus nerve.

An additional object of the invention is to provide a forceps suited for excellent characteristics for use in operations involving the vagus nerve by virtue of added length to the forceps handle.

A still further object of the invention to provide a forceps having a grasping opening, as opposed to a clamping opening, of a size and shape which prevents crushing of the vagus nerve during interventions in the lower esophagus or stomach.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
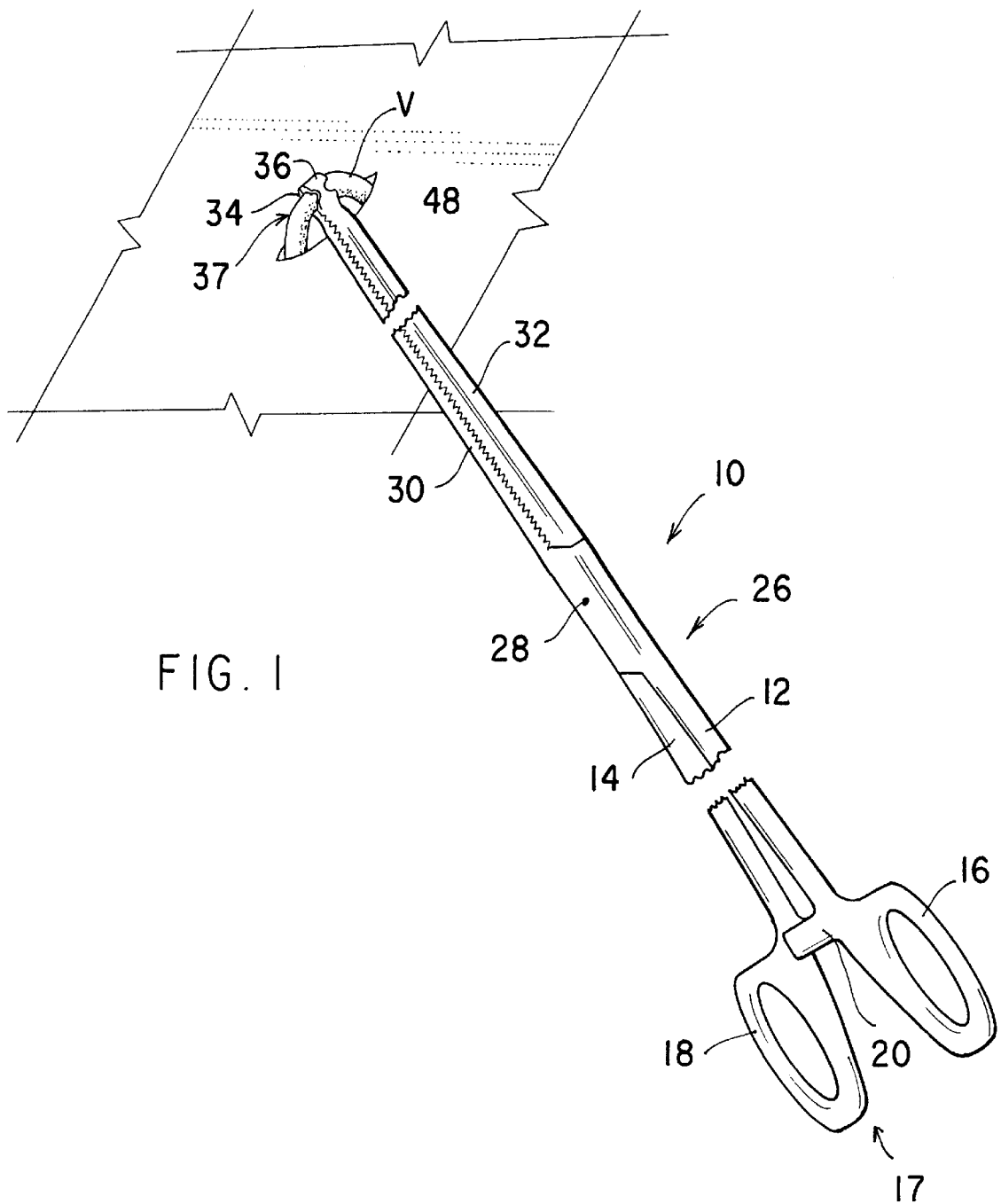
FIG. 1 is an environmental, perspective view of a forceps according to the present invention.

The present invention is a surgical instrument for grasping, elevating, and retracting stranded or tubular tissue, particularly the vagus nerve. Referring to FIGS. 1–5, a forceps 10 includes arms 12, 14, each having handle sections 16, 18 at a first end 17. The handle sections 16, 18 have sawtooth extensions 20, 22 projecting inward from the handle sections 16, 18. The sawtooth extensions 20, 22 engage one another when the forceps 10 is in a closed position, as shown in FIG. 2A.

The arms 12, 14 also have pivoting sections 24, 26 next to the handle sections 16, 18. Along these pivoting sections 24, 26, the arms 12, 14 cross one another and are connected at their crossing by a cross-over stud 28, as shown in FIG. 1. The preferred length between stud 28 and first end 17 is approximately 14.5 centimeters. The length from stud 28 to a second end 19 is approximately 8 centimeters. The arms 12,14 of the forceps 10 approximate eleven centimeters from stud 28. An overall length of the forceps 10 of approximately 22.5 centimeters is thereby attained, providing additional reach necessary in surgical interventions in the lower esophagus and stomach where the vagus is present.

The arms 12, 14 additionally have grasping sections 30, 32 at a second end 19. These grasping sections 30, 32 comprise grasping tips 34, 36 which define and semi-enclose open, grasping regions 38, 40. As may be seen, from FIG. 2A particularly, the juxtaposition of such grasping regions 38, 40 upon placement of the forceps 10 in a closed orientation, forms a substantially oval opening 42, somewhat elongated along an axis parallel to a long axis of the forceps. Sample dimensions for the opening are 0.3 centimeters in width and 0.4 centimeters in length (or 3 mm transverse inner diameter and 4 mm longitudinal inner diameter).

Figures 2A, 2B:
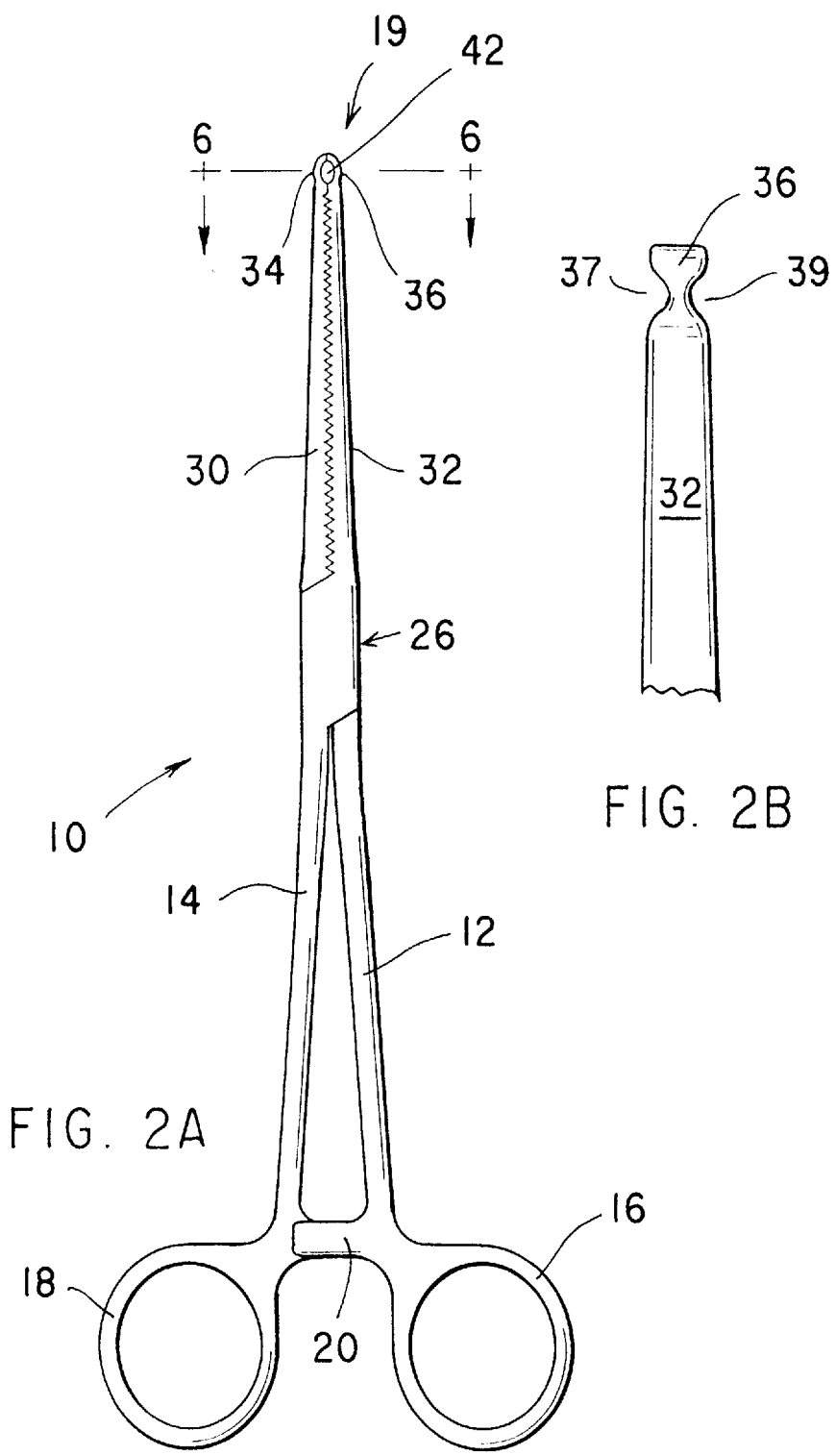
FIG. 2A is an top plan view of the forceps in a closed state according to the present invention.
FIG. 2B is a side view of a partial profile of the forceps according to the present invention, featuring the hourglass profile of the closed tip.
Figure 3:
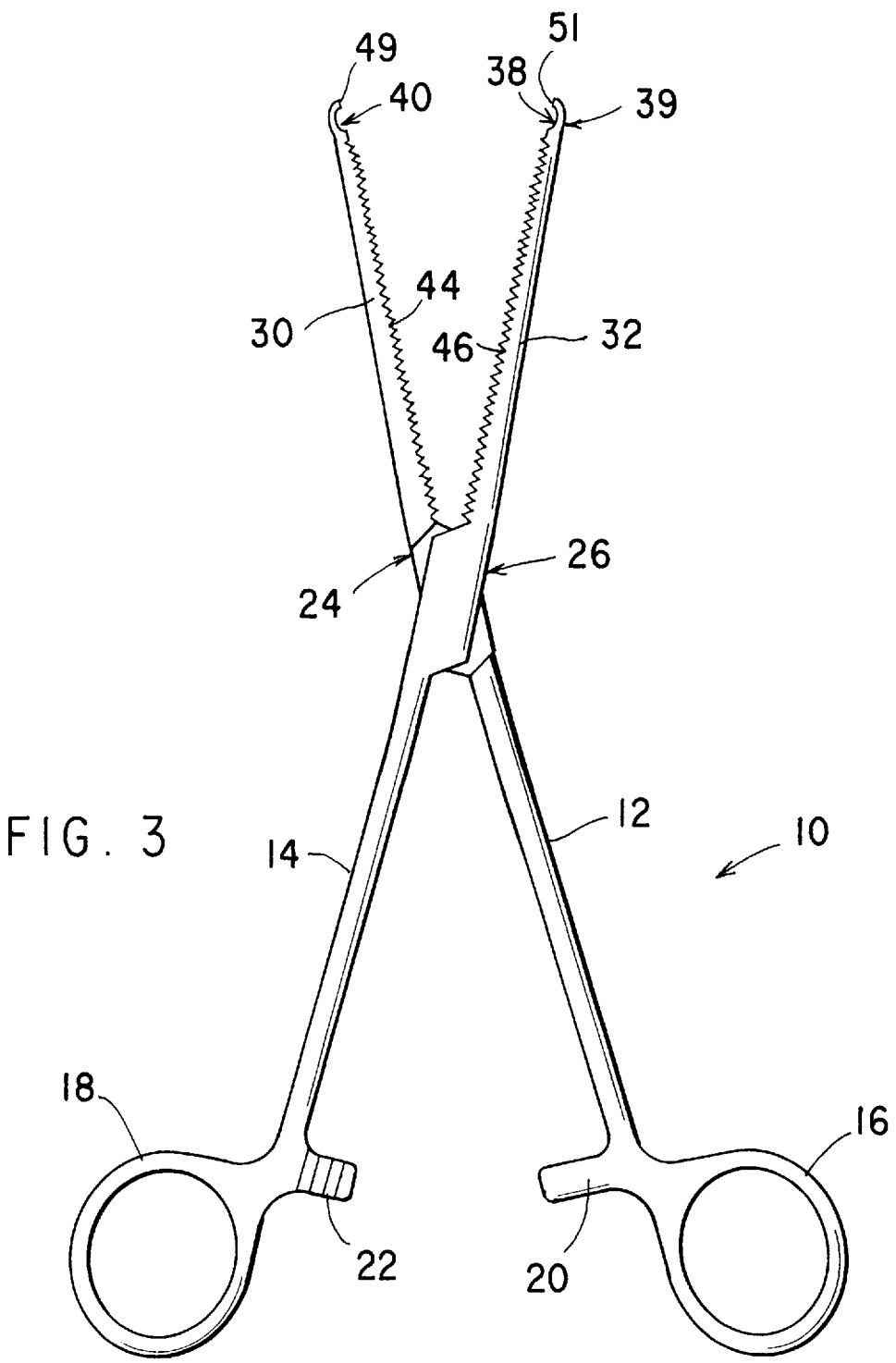
FIG. 3 is a top plan view of a partial profile of the forceps in an open state according to the present invention.
Figure 4:
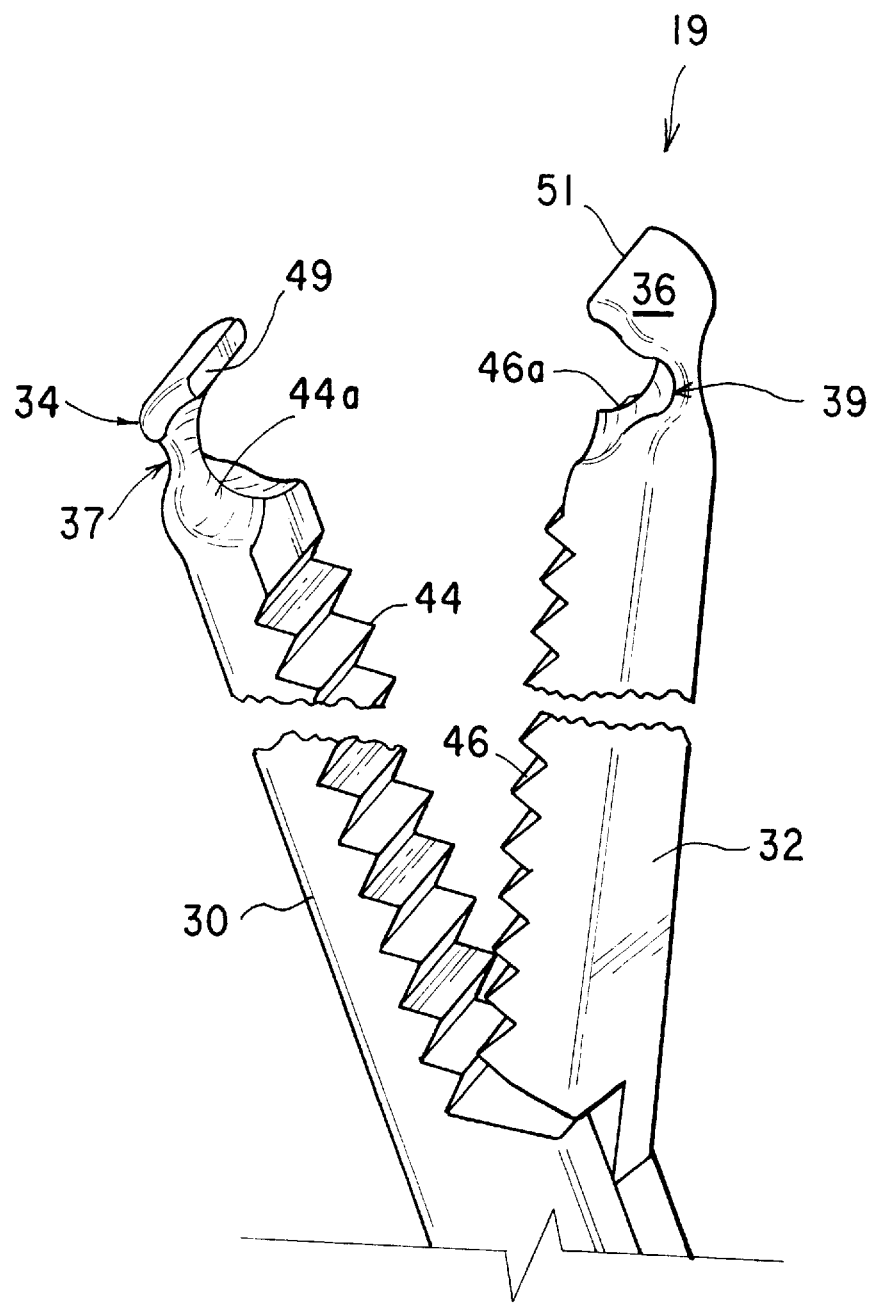
FIG. 4 is a greatly enlarged, perspective view of a detail of the forceps according to the present invention, featuring the open tip.
Figure 6:
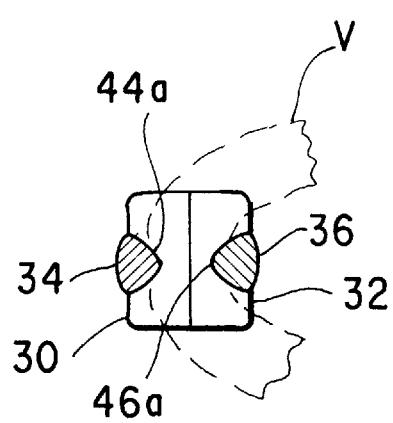
FIG. 6 is a top view of the forceps according to the present invention, environmentally representing the vagus nerve enclosed in the grasping tips, as drawn along line 6—6 of FIG. 2A.
Figure 5:
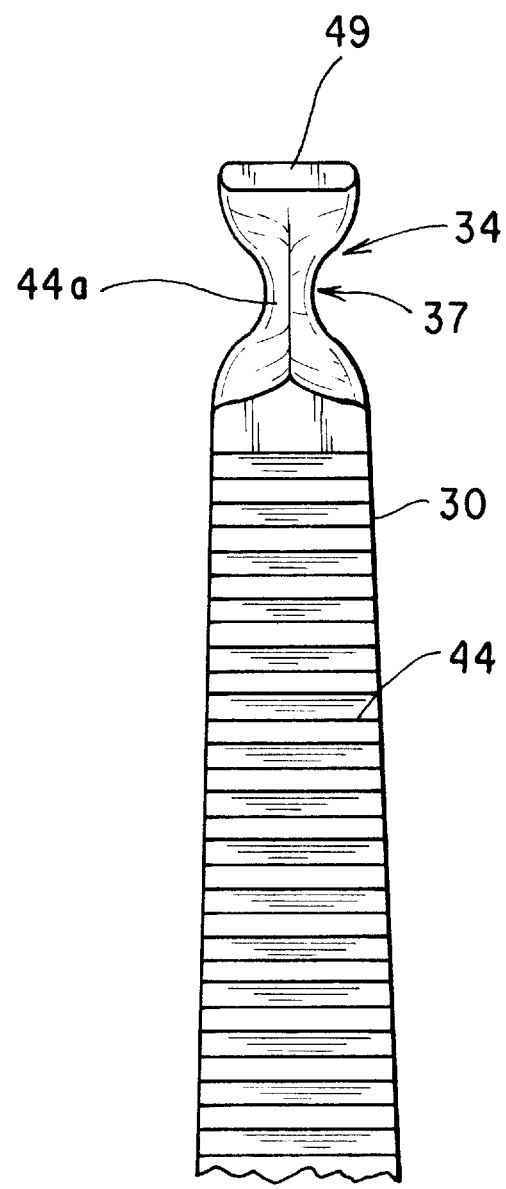
FIG. 5 is a side view, partially fragmented of the forceps according to the present invention, featuring the hourglass profile of the closed tip.

In profile, grasping tips 34,36 are both formed as identical hourglass configurations, which provide opposing, transverse grooves 37,39, as most clearly seen in FIG. 2B. As shown in FIG. 1, the hourglass profile allows the vagus nerve V to rest in a transverse groove 37 of a grasping tip 34, providing a seat minimizing pinching and crushing of the nerve when stretched during retraction. As can be appreciated from FIG. 6, the vagus nerve V is shown closely entrapped by the grasping tips 34,36, and grooves 37,39 of tip 36 permit a gradual bend in the vagus nerve without pinching, unlike a cylindrical channel formed by a edge over which the vagus nerve could be pinched. As a further result of the hourglass configuration, the leading edges 49,51 (FIGS. 3 and 4) appear as bar-like edges, having a nominal width and a length substantially the same as the thickness of the instrument. The nominal width minimizes the surface area capable of inadvertently grasping surrounding tissue but still allows edges 49,51 to completely enclose the vagus nerve.

The grasping sections 30, 32 also have mating serrations 44, 46, which lie farther from the second end than the grasping tips 34, 36 and grasping regions 38, 40, and immediately adjacent to said tips 34, 36 and said regions 38, 40. These serrations 44, 46 facilitate the grasping function of the forceps 10 by forming a line following the lengthwise extension of the instrument as shown in FIGS. 1 and 2A, to provide a continuous, firmly closed line behind the grasping tips 34,36, which line defines in part the longitudinal axis of the forceps 10.

The grasping tips 34, 36 have a v-shape formed by inverted v-shaped beveled surfaces extending away from arms 12, 14 into oval opening 42. The v-shaped surfaces or ridges 44a, 46a (best viewed in FIG. 4) are disposed circumferentially around inner edges or facing surface of the grasping tips 34, 36. The v-shaped surfaces 44a, 46a may extend along the entire facing surfaces of grasping tips 34, 36 or may extend only partially along the facing surfaces, preferably along the lower half of the facing surfaces closer to the first end 17. The v-shaped ridges project at a greater height at an end of the grasping tips 34, 36 farther from the second end 19 than at an end of the grasping tips 34, 36 nearer to the second end 19. The v-shaped ridges 44a, 46a culminate in crest tips. The crest tips may be sharp or may be rounded, preferably with a radius of curvature of about 500 micrometers. Again referring to FIG. 6, the v-shaped surfaces facilitate the grasping function of the forceps 10 by slightly circumferentially depressing the vagus nerve without crushing, and thereby preventing lateral sliding of the forceps.

Because of the compact and efficient shape of the present forceps 10, an incision 48 of surrounding connective tissue can be smaller than an incision (not shown) provided using forceps of the prior art (not shown). More specifically, the grasping tips 34, 36 are extraordinarily narrow, as viewed from any perspective, FIGS. 1 and 5. Additionally, the grasping regions 38, 40 are positioned at a most extreme portion of the second end 19, so that there is essentially no distance between the grasping regions 38, 40 and the most extreme portion of the second end 19, as exemplified in FIG. 4 by the narrow width of the leading edge 49. As will be appreciated, limitations on the character of submitted drawings make it necessary to depict even very thin objects with with some distance between edges; however, it must be understood that the locations of the grasping regions 38, 40 are as close to the most extreme portion of the second end 19 as is physically and practically possible. This positioning of the grasping regions 38, 40 comprise a crux of the innovation of this invention, insofar as this positioning enables the user to grasp tubular tissue such as the vagus nerve V without contacting or grasping tissue beyond the location of the tubular tissue sought to be grasped, and without making a large incision.

With more particularity, the dimensions of the generally oval shaped opening 42 are about 0.40 centimeters in length and 0.30 centimeters in width, and the distance between the most extreme portion of the second end 19 of arms 12, 14, and the end of the opening nearest the tip is less than 1 millimeter. These dimensions are depicted approximately in FIGS. 2A and 3, within the constraints of limitations on submitted drawings. It may be seen particularly from FIG. 3, that the size of the elongated overall grasping sections 30, 32, the closed loop or oval opening 42, and the proximity of this loop 42 to the distal extremity of the forcep arms 12, 14 enables the use and advantages of the present forceps 10 with the procedures retracting the vagus nerve. Moreover, the small size and extreme location of the grasping sections 30, 32 and the closed loop 42, as well as the proximity of this end loop to the distal extremity of the forcep arms 12, 14, enable the user to efficiently tip up or lift the vagus nerve 52 to be out of the incision 48, i.e. retraction. The overall procedure is thereby enabled with a greatly shortened time for the surgery, and with more precision in lifting and initially locating the vagus nerve. In other words, the shape and size of the grasping sections 30, 32 permit the user to firmly grasp the vagus nerve V, to lift it up and out of the incision 48, and thus exposing the surrounding area for further manipulation. Significantly, the risk of slippage of the vagus V, when it is held by the forceps 10 is greatly reduced. The mating serrations, forming a line matching the lengthwise extension of the instrument, closes firmly behind the opening.

It is to be understood that the present invention is not limited to the embodiments described above, but encompasses any and all embodiments within the scope of the following claims.

I claim:

1. A forceps for use with the vagus nerve of a human body comprising:
   a pair of elongated forceps arms, one elongated arm having an aperture therethrough, a first end at least 10.5 centimeters from the aperture, and a second end at least 3 centimeters from the aperture;
   a stud disposed wholly within the aperture of said one elongated arm, said stud pivotally connecting said pair of elongated arms;
   a handle formed at the first end of each elongated arm; and,
   a grasping section formed at the second end of each elongated arm, each said grasping section terminating in a grasping tip, each said grasping tips together positioned opposite one another and defining an oval opening when said forceps are closed, said opening being not more than 0.40 centimeters in diameter in a first direction parallel with said elongated arms and not more than 0.30 centimeters in diameter in a direction substantially perpendicular in two axes to said first direction, said opening disposed within one millimeter of the second end of said elongated arms, each said grasping tip having a v-shaped ridge, each said v-shaped ridge together being diametrically opposed and disposed within said oval opening, and said grasping section also including a serrated portion adjacent to said grasping tip.

2. The forceps according to claim 1, wherein said arms from said rod to said handle are at least 10 centimeters.

3. The forceps according to claim 1 wherein said first end is approximately 14.5 centimeters from said aperture.

4. The forceps according to claim 1, wherein said arms from said rod to said handle are approximately 11 centimeters in length.

5. The forceps according to claim 1 wherein said v-shaped grasping tips terminate in a sharp edge.

6. The forceps according to claim 1 wherein said v-shaped grasping tips terminate in a rounded edge having a radius of curvature of about 500 micrometers.

7. The forceps according to claim 1 wherein each said v-shaped grasping tip includes a groove transverse to the direction of said elongated arms, each said groove aligning coextensively with an opposing groove on the other of said tips.

8. The forceps according to claim 7 wherein said grasping tips have opposing outer faces and a second groove is provided in a parallel plane and on each said opposing outer face of each said grasping tip.

* * * * *